United States Patent
Wilk

(10) Patent No.: US 7,511,071 B2
(45) Date of Patent: Mar. 31, 2009

(54) THIOAMIDE DERIVATIVES AS PROGESTERONE RECEPTOR MODULATORS

(75) Inventor: Bogdan Kazimierz Wilk, New City, NY (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 12/044,287

(22) Filed: Mar. 7, 2008

(65) Prior Publication Data

US 2008/0167299 A1 Jul. 10, 2008

Related U.S. Application Data

(62) Division of application No. 11/100,860, filed on Apr. 7, 2005, now Pat. No. 7,358,246.

(60) Provisional application No. 60/560,569, filed on Apr. 8, 2004.

(51) Int. Cl.
*C07D 417/10* (2006.01)
*C07D 417/14* (2006.01)
*A61K 31/5415* (2006.01)
*A61K 31/547* (2006.01)

(52) U.S. Cl. ..................... 514/414; 548/466
(58) Field of Classification Search ................. 548/466; 514/414
See application file for complete search history.

(56) References Cited

U.S. PATENT DOCUMENTS

| | | |
|---|---|---|
| 3,536,809 A | 10/1970 | Applezweig |
| 3,598,123 A | 8/1971 | Zaffaroni |
| 3,845,770 A | 11/1974 | Theeuwes et al. |
| 3,916,899 A | 11/1975 | Theeuwes et al. |
| 4,008,719 A | 2/1977 | Theeuwes et al. |
| 4,295,987 A | 10/1981 | Parks |
| 4,959,217 A | 9/1990 | Sanders et al. |
| 5,124,455 A | 6/1992 | Lombardo |
| 5,273,752 A | 12/1993 | Ayer et al. |
| 5,459,151 A | 10/1995 | Lombardo |
| 5,756,127 A | 5/1998 | Grisoni et al. |
| 5,817,343 A | 10/1998 | Burke |
| 5,854,388 A | 12/1998 | Harding et al. |
| 6,391,907 B1 | 5/2002 | Fensome et al. |
| 6,407,101 B1 | 6/2002 | Collins et al. |
| 6,417,214 B1 | 7/2002 | Ullrich et al. |
| 6,436,929 B1 | 8/2002 | Zhang et al. |
| 6,509,334 B1 | 1/2003 | Zhang et al. |
| 6,518,306 B1 | 2/2003 | Christensen |
| 6,716,871 B2 | 4/2004 | Martins et al. |
| 7,115,649 B2 | 10/2006 | Fensome et al. |
| 7,122,705 B2 | 10/2006 | Wilk |
| 7,192,956 B2 | 3/2007 | Fensome et al. |
| 7,268,149 B2 | 9/2007 | Fensome et al. |
| 7,314,932 B2 | 1/2008 | Wilk |
| 2004/0002535 A1 | 1/2004 | Fensome et al. |
| 2005/0227971 A1 | 10/2005 | Wilk |
| 2005/0250766 A1 | 11/2005 | Wilk |

FOREIGN PATENT DOCUMENTS

| | | |
|---|---|---|
| EP | 314206 | 10/1993 |
| WO | WO 98/44964 | 10/1998 |
| WO | WO 00/66581 | 11/2000 |
| WO | WO 04/000230 | 12/2003 |
| WO | WO 04/000801 | 12/2003 |
| WO | WO 2004/000225 | 12/2003 |
| WO | WO 2004/000227 | 12/2003 |

OTHER PUBLICATIONS

Fensome, "Novel 5-aryl-1,3-dihydro-indole-2-thiones. potent, orally active progesterone receptor agonists", Bioorganic & Medicinal Chemistry Letters, 13(7):1317-1320, (Apr. 7, 2003).

Testa, "Prodrugs revisited: the "ad hoc" approach as a complement to ligand design", Medicinal Research Reviews, 16(3):233-241 (May 1996).

*Primary Examiner*—Kahsay T Habte
(74) *Attorney, Agent, or Firm*—Paul Carango; Howson & Howson LLP

(57) ABSTRACT

Thioamide compounds, and specifically, thioamide pyrrole compounds, and preparation thereof are provided. These thioamide compounds can be used as progesterone receptor modulators, in contraception, and in the treatment of progesterone-related maladies.

19 Claims, No Drawings

THIOAMIDE DERIVATIVES AS PROGESTERONE RECEPTOR MODULATORS

CROSS-REFERENCE TO RELATED APPLICATIONS

This application is a divisional of U.S. patent application Ser. No. 11/100,860, filed Apr. 7, 2005, which claims the benefit under 35 USC 119(e) of prior U.S. Provisional Patent Application No. 60/560,569, filed Apr. 8, 2004, now abandoned.

BACKGROUND OF THE INVENTION

The present invention relates to progesterone receptor modulators.

Intracellular receptors (ER) form a class of structurally related gene regulators known as "ligand dependent transcription factors". The steroid receptor family is a subset of the IR family, including progesterone receptor (PR), estrogen receptor (ER), androgen receptor (AR), glucocorticoid receptor (GR), and mineralocorticoid receptor (MR). A compound that binds to an IR and mimics the action of the natural hormone is termed an agonist, whilst a compound that inhibits the effect of the hormone is an antagonist.

The natural hormone, or ligand, for the PR is the steroid progesterone, but synthetic compounds, such as medroxyprogesterone acetate or levonorgestrel, have been made which also serve as ligands. Once a ligand is present in the fluid surrounding a cell, it passes through the membrane via passive diffusion, and binds to the IR to create a receptor/ligand complex. This complex binds to specific gene promoters present in the cell's DNA. Once bound to the DNA the complex modulates the production of mRNA and protein encoded by that gene.

PR agonists (natural and synthetic) are known to play an important role in the health of women. PR agonists are used in birth control formulations, typically in the presence of ER agonists, alternatively they may be used in conjunction with PR antagonists. ER agonists are used to treat the symptoms of menopause, but have been associated with a proliferative effect on the uterus that can lead to an increased risk of uterine cancers. Co-administration of a PR agonist reduces or ablates that risk.

U.S. Pat. No. 6,407,101, which is hereby incorporated by reference, describes the preparation of cyclocarbamate derivatives, which are useful as progesterone receptor modulators. These cyclocarbamate derivatives, including, e.g., 5-(4,4-dimethyl-2-thioxo-1,4-dihydro-2H-benzoxazin-6-yl)-1-methyl-1H-2-cyano-pyrrole, are prepared by thionation of the corresponding benzoxazin-2-one (Scheme 1).

Scheme 1

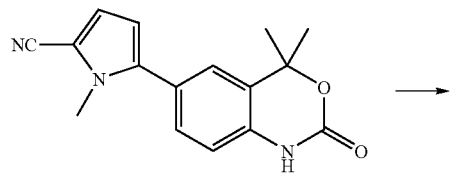

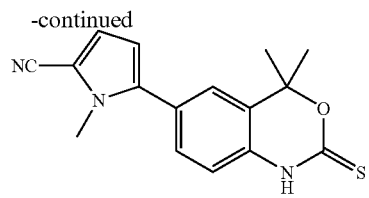

What is needed in the art are alternate compounds that are effective as progesterone receptor modulators.

SUMMARY OF THE INVENTION

In one aspect, the present invention provides a compound of formula I of the structure:

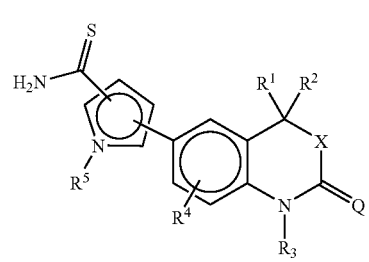

In another aspect, the present invention provides the compounds 5-(4,4-dimethyl-2-thioxo-1,4-dihydro-2H-3,1-benzoxazin-6-yl)-1-methyl-1H-pyrrole-2-carbothioamide, 5-(4,4-dimethyl-2-oxo-1,4-dihydro-2H-3,1-benzoxazin-6-yl)-1-methyl-1H-pyrrole-2-carbothioamide, 5-(2'-thioxospiro[cyclohexane-1,3'-[3H]-indol]-5'-yl)-1-methyl-1H-pyrrole-2-carbothioamide, or a pharmaceutically acceptable salt thereof.

In a further aspect, the present invention provides pharmaceutical compositions containing compounds of the invention, or a pharmaceutically acceptable salt thereof, for use in contraception; hormone replacement therapy; treating or preventing hormone-dependent neoplastic disease; treating dysfunctional bleeding, uterine leiomyomata, endometriosis, or polycystic ovary syndrome; synchronizing estrus; treating acne; or treating hirsutism.

In yet another aspect, the present invention provides use of compounds of the invention in preparing a medicament useful in contraception; hormone replacement therapy; treating or preventing hormone-dependent neoplastic disease; treating dysfunctional bleeding, uterine leiomyomata, endometriosis, or polycystic ovary syndrome; synchronizing estrus; treating acne; or treating hirsutism; in a mammal in need thereof.

In still another aspect, the present invention provides pharmaceutical kits or packs containing a course of treatment for contraception; hormone replacement therapy; treating or preventing hormone-dependent neoplastic disease; treating dysfunctional bleeding, uterine leiomyomata, endometriosis, or polycystic ovary syndrome; synchronizing estrus; treating acne; or treating hirsutism, comprising a container having a compound or composition of the invention in unit dosage form.

In yet another aspect, the present invention provides methods for preparing compounds of the invention.

Other aspects and advantages of the present invention are described further in the following detailed description of the preferred embodiments thereof.

DETAILED DESCRIPTION OF THE INVENTION

The present invention provides novel progesterone receptor modulators, including thioamide compounds, and methods for preparing the same. The thioamide compounds of the invention are useful for a variety of purposes including use as progesterone receptor modulators, and specifically for contraception; hormone replacement therapy; treating or preventing hormone-dependent neoplastic disease; treating dysfunctional bleeding, uterine leiomyomata, endometriosis, or polycystic ovary syndrome; synchronizing estrus; treating acne; or treating hirsutism by administering the compounds of the invention to a mammal in need thereof.

I. Definitions

The term "alkyl" is used herein to refer to both straight- and branched-chain saturated aliphatic hydrocarbon groups having 1 to about 10 carbon atoms, or 1 to about 8 carbon atoms. The term "alkenyl" is used herein to refer to both straight- and branched-chain alkyl groups having one or more carbon-carbon double bonds and containing about 2 to about 10 carbon atoms. In one embodiment, the term alkenyl refers to an alkyl group having 1 or 2 carbon-carbon double bonds and having 2 to about 6 carbon atoms. The term "alkynyl" is used herein to refer to both straight- and branched-chain alkyl groups having one or more carbon-carbon triple bond and having 2 to about 8 carbon atoms. In one embodiment, the term alkynyl refers to an alkyl group having 1 or 2 carbon-carbon triple bonds and having 2 to about 6 carbon atoms.

The term "cycloalkyl" is used herein to refer to an alkyl group as previously described that is cyclic in structure and has about 4 to about 10 carbon atoms, or about 5 to about 8 carbon atoms.

The terms "substituted alkyl", "substituted alkenyl", "substituted alkynyl", and "substituted cycloalkyl" refer to alkyl, alkenyl, alkynyl, and cycloalkyl groups, respectively, having one or more substituents including, without limitation, halogen, CN, OH, $NO_2$, amino, aryl, heterocyclic, alkoxy, aryloxy, alkylcarbonyl, alkylcarboxy, and arylthio which groups can be optionally substituted. These substituents can be attached to any carbon of an alkyl, alkenyl, or alkynyl group provided that the attachment constitutes a stable chemical moiety.

The term "aryl" as used herein refers to an aromatic system which can include a single ring or multiple aromatic rings fused or linked together where at least one part of the fused or linked rings forms the conjugated aromatic system. The aryl groups can include, but are not limited to, phenyl, naphthyl, biphenyl, anthryl, tetrahydronaphthyl, phenanthryl, indene, benzonaphthyl, and fluorenyl.

The term "substituted aryl" refers to an aryl group which is substituted with one or more substituents including halogen, CN, OH, $NO_2$, amino, alkyl, cycloalkyl, alkenyl, alkynyl, alkoxy, aryloxy, alkyloxy, alkylcarbonyl, alkylcarboxy, aminoalkyl, and arylthio, which groups can be optionally substituted. In one embodiment, a substituted aryl group is substituted with 1 to about 4 substituents.

The term "heterocyclic" as used herein refers to a stable 4- to 7-membered monocyclic or multicyclic heterocyclic ring which is saturated, partially unsaturated, or wholly unsaturated. The heterocyclic ring has carbon atoms and one or more heteroatoms including nitrogen, oxygen, and sulfur atoms. In one embodiment, the heterocyclic ring has 1 to about 4 heteroatoms in the backbone of the ring. When the heterocyclic ring contains nitrogen or sulfur atoms in the backbone of the ring, the nitrogen or sulfur atoms can be oxidized. The term "heterocyclic" also refers to multicyclic rings in which a heterocyclic ring is fused to an aryl ring. The heterocyclic ring can be attached to the aryl ring through a heteroatom or carbon atom provided the resultant heterocyclic ring structure is chemically stable.

A variety of heterocyclic groups are known in the art and include, without limitation, oxygen-containing rings, nitrogen-containing rings, sulfur-containing rings, mixed heteroatom-containing rings, fused heteroatom containing rings, and combinations thereof. Oxygen-containing rings include, but are not limited to, furyl, tetrahydrofuranyl, pyranyl, pyronyl, and dioxinyl rings. Nitrogen-containing rings include, without limitation, pyrrolyl, pyrazolyl, imidazolyl, triazolyl, pyridyl, piperidinyl, 2-oxopiperidinyl, pyridazinyl, pyrimidinyl, pyrazinyl, piperazinyl, azepinyl, triazinyl, pyrrolidinyl, carbazolyl, and azepinyl rings. Sulfur-containing rings include, without limitation, thienyl and dithiolyl rings. Mixed heteroatom containing rings include, but are not limited to, oxathiolyl, oxazolyl, thiazolyl, oxadiazolyl, oxatriazolyl, dioxazolyl, oxathiazolyl, oxathiolyl, oxazinyl, oxathiazinyl, morpholinyl, thiamorpholinyl, thiamorpholinyl sulfoxide, oxepinyl, thiepinyl, and diazepinyl rings. Fused heteroatom-containing rings include, but are not limited to, benzofuranyl, thionapthene, indolyl, benazazolyl, purindinyl, pyranopyrrolyl, isoindazolyl, indoxazinyl, benzoxazolyl, anthranilyl, benzopyranyl, quinolinyl, isoquinolinyl, benzodiazonyl, napthylridinyl, benzothienyl, pyridopyridinyl, benzoxazinyl, xanthenyl, acridinyl, and purinyl rings.

The term "substituted heterocyclic" as used herein refers to a heterocyclic group having one or more substituents including halogen, CN, OH, $NO_2$, amino, alkyl, cycloalkyl, alkenyl, alkynyl, alkoxy, aryloxy, alkyloxy, alkylcarbonyl, alkylcarboxy, aminoalkyl, and arylthio, which groups can be optionally substituted. In one embodiment, a substituted heterocyclic group is substituted with 1 to about 4 substituents.

The term "alkoxy" as used herein refers to the O(alkyl) group, where the point of attachment is through the oxygen-atom and the alkyl group is optionally substituted.

The term "aryloxy" as used herein refers to the O(aryl) group, where the point of attachment is through the oxygen-atom and the aryl group is optionally substituted.

The term "alkyloxy" includes hydroxyalkyl and as used herein refers to the alkyl OH group, where the point of attachment is through the alkyl group.

The term "arylthio" as used herein refers to the S(aryl) group, where the point of attachment is through the sulfur-atom and the aryl group can be optionally substituted.

The term "alkylcarbonyl" as used herein refers to the C(O)(alkyl) group, where the point of attachment is through the carbon-atom of the carbonyl moiety and the alkyl group is optionally substituted.

The term "alkylcarboxy" as used herein refers to the C(O)O(alkyl) group, where the point of attachment is through the carbon-atom of the carboxy moiety and the alkyl group is optionally substituted.

The term "aminoalkyl" includes alkylamino and as used herein refers to both secondary and tertiary amines where the point of attachment is through the nitrogen-atom and the alkyl groups are optionally substituted. The alkyl groups can be the same or different.

The term "thioalkoxy" or "thioalkyl" as used herein refers to the S(alkyl), where the point of attachment is through the sulfur-atom and the alkyl group is optionally substituted.

The term "halogen" as used herein refers to Cl, Br, F, or I groups.

The term "acne" is meant to include any skin disorder where a skin pore becomes blocked and/or thereby becomes inflamed. The term acne includes without limitation superficial acne, including comedones, inflamed papules, superficial cysts, and pustules; and deep acne, including deep inflamed modules and pus-filled cysts. Specific acne conditions can include, but are not limited to, acne vulgaris, acne comedo, papular acne, premenstrual acne, preadolescent acne, acne venenata, acne cosmetica, pomade acne, acne detergicans, acne excoriee, gram negative acne, acne rosacea, pseudofolliculitis barbae, folliculitis, perioral dermatitis, and hiddradenitis suppurativa.

The term "hirsutism" is meant to describe a skin disorder where an overgrowth of hair growth is observed in areas of the body which are not normally subject to excessive hair growth.

The term "selective estrogen receptor modulator" or "SERM" is meant to describe a compound that exhibits activity as an agonist or antagonist of an estrogen receptor in a tissue-dependent manner. SERMs can act as estrogen receptor agonists in some tissues and as antagonists in other tissue types. The term SERMs can also be interchanged with the term "anti-estrogen".

II. Compounds of the Invention

The present invention therefore provides for compounds of formula I of the structure:

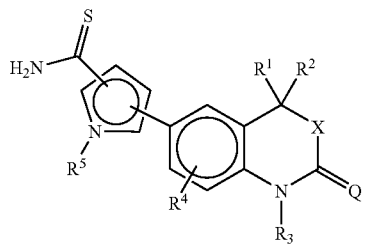

I wherein, $R^1$ and $R^2$ can be, independently, H, $C_1$ to $C_6$ alkyl, or substituted $C_1$ to $C_6$ alkyl. $R^1$ and $R^2$ can also be fused to form a ring including —$CH_2(CH_2)_nCH_2$—, —$CH_2CH_2C(CH_3)_2CH_2CH_2$—, —$O(CH_2)_pCH_2$—, —$O(CH_2)_qO$—, —$CH_2CH_2OCH_2CH_2$—, or —$CH_2CH_2NR^6CH_2CH_2$—, where n is 1 to 5; p is 1 to 4; and q is 1 to 4. $R^3$ can be H, OH, $NH_2$, CN, halogen, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, or $COR^A$. $R^4$ can be H, $C_1$ to $C_6$ alkyl, substituted $C_1$ to $C_6$ alkyl, $C_1$ to $C_6$ alkoxy, substituted $C_1$ to $C_6$ alkoxy, $C_1$ to $C_6$ aminoalkyl, or substituted $C_1$ to $C_6$ aminoalkyl. $R^4$ can be H, $C_1$ to $C_6$ alkyl, substituted $C_1$ to $C_6$ alkyl, $C_1$ to $C_6$ alkoxy, substituted $C_1$ to $C_6$ alkoxy, $C_1$ to $C_6$ aminoalkyl, or substituted $C_1$ to $C_6$ aminoalkyl. $R^5$ can be $C_1$ to $C_6$ alkyl, substituted $C_1$ to $C_6$ alkyl, or $COR^A$. $R^6$ can be H or $C_1$ to $C_6$ alkyl. X can be O, S, or absent. Q can be O or S.

The present invention also provides for compounds of formula I, where $R^1$ and $R^2$ are $C_1$ to $C_6$ alkyl, $R^3$ is H, $R^4$ is H, and $R^5$ is $C_1$ to $C_6$ alkyl.

In one embodiment, the present invention provides for compounds of the following formulae, where $R^1$-$R^3$ and $R^5$ are defined as described above.

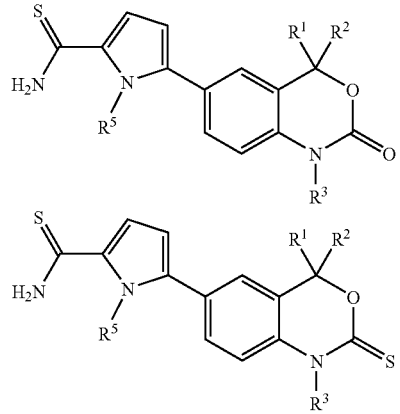

In another embodiment, the present invention provides the following compounds:

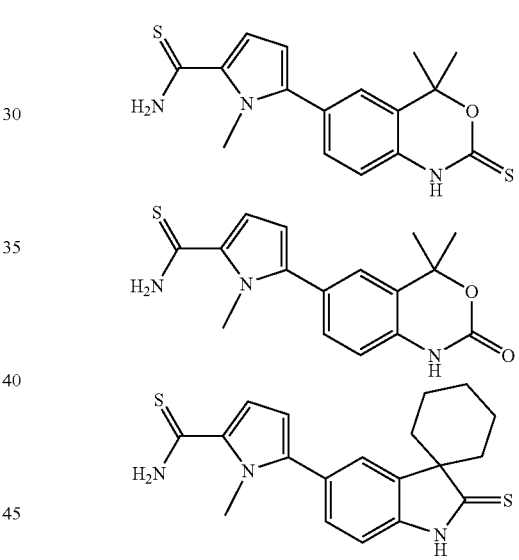

Examples of $R^1$ and $R^2$ are $CH_3$, or $R^1$ and $R^2$ are fused to form a ring comprising —$CH_2(CH_2)_nCH_2$—. An example of n is 3.

An example of $R^3$ is H. $R^4$ may be for example H.

An example of $R^5$ is $CH_3$.

Q may be O in some embodiments or Q is S in other embodiments.

An example of X is O. In other embodiments X is absent.

The pyrrole ring may be for example 2,5-disubstituted.

III. Methods for Preparing Thioamides

The thioamides of the present invention can be prepared by reacting a compound containing a CN moiety with a sulfur-containing agent in the presence of a base. The compounds containing the CN moieties can have substituents other than CN moieties. Examples of compounds containing CN moieties and other optional substituents include compounds of formula II, wherein $R^1$—$R^5$, Q, and X are defined as described above. In one embodiment, the compound containing the CN moiety contains a pyrrole group containing one or more CN substituents attached to the pyrrole ring. In another embodiment, the CN moiety is attached at the 2-position, 3-position, or 4-position of the pyrrole ring. In yet another embodiment, the CN moiety is attached at the 2-position of the ring. However, the location and number of CN moieties is not a limitation of the present invention.

The thioamides of the present invention can be prepared by reacting the cyanopyrrole compound with a sulfur-containing agent, in the presence of a solvent and a base, optionally in the presence of heat, (based on procedure by R. Shabana, H. J. Meyer, S.-O. Lawesson *Phosphorus and Sulfur* 1985, 25, 297).

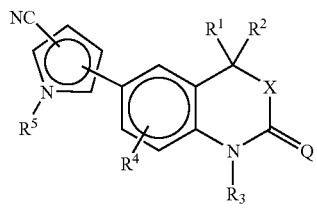

II

The solvent can include any reagent that does not react with the components of the reaction mixture and includes ethers. In one embodiment, the solvent is 1,2-dimethoxyethane (DME), tetrahydrofuran (THF) or diethylether. In another embodiment, the solvent is DME. The solvent can also include other agents that do not interfere with the reaction and includes, without limitation, water or alcohols.

The sulfur-containing agent must be capable of reacting with the nitrile moiety of the pyrrole group and includes, without limitation, a dialkyldithiophosphate, a diaryldithiophosphate, hydrogen sulfide ($H_2S$), 2,4-bis(4-methoxyphenyl)-1,3-dithia-2,4-diphosphetane-2,4-disulfide (Lawesson's reagent), or phosphorus pentasulfide. In one embodiment, the sulfur-containing agent is a dialkyldithiophosphate or diaryldithiophosphate. In another embodiment, the sulfur-containing agent is diethyldithiophosphate.

In one embodiment, a 1:1 ratio of sulfur-containing agent to the compound of formula II in the range of 1:1 to 3:1 is utilized. One of skill in the art would readily be able to determine the amount of sulfur-containing agent to utilize depending on the reaction conditions, reagents, and purification required. For example a ratio of about 1:1, about 1.5:1, about 2:1 ratio, about 2.5:1, or about 3:1 can be used.

The base utilized according to the present invention can be an amine. In one embodiment, the amine is an alkylated amine including N,N-diisopropylethylamine (Hünig's base), triethylamine, and pyridine, among others. Only catalytic amounts of the base are required, but greater amounts of the same can be utilized and can be readily determined by one of skill in the art.

The thioamides of the present invention can be formed by the addition of hydrogen sulfide ($H_2S$) or Lawesson's reagent derivatives to the nitrile moiety of the cyanopyrrole group. The $H_2S$ can result from the hydrolysis of Lawesson's reagent or phosphorus pentasulfide by water. The $H_2S$ can also be formed by reaction of any alcohol, including methanol (MeOH) or isopropanol (iPrOH) that is present in the solvent, with Lawesson's reagent to give O-esters of phosphonodithioic acid and $H_2S$.

The compounds of formula I can be purified using techniques known to those of skill in the art and include, without limitation, extraction, recrystallization, chromatography, precipitation, and distillation. In one embodiment, the compound of formula I is purified by dissolving the compound of formula I in a dissolving solvent to form a solution. The dissolving solvent can include any solvent that dissolves the compound of formula I with or without heating the same. The selection of the dissolving solvent can be readily determined by one of skill in the art. In another embodiment, the dissolving solvent is acetone, 2-butanone, tetrahydrofuran, or DME. In yet another embodiment, the solvent is acetone, or acetone heated to its boiling point. The dissolving solvent containing the compound of formula I can then be concentrated by distillation or vacuum. In still another embodiment, the dissolving solvent containing the compound of formula I is concentrated by distillation. Thereafter, purified compound of formula I is isolated by precipitation, optionally by cooling the concentrated dissolving solvent.

In one embodiment, the present invention provides a method for preparing a compound of formula I of the structure:

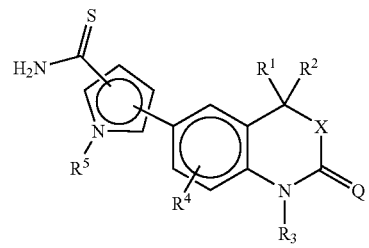

I wherein, $R^1$ and $R^2$ can be, independently, H, $C_1$ to $C_6$ alkyl, or substituted $C_1$ to $C_6$ alkyl. $R^1$ and $R^2$ can also be fused to form a ring including —$CH_2(CH_2)_nCH_2$—, —$CH_2CH_2C(CH_3)_2CH_2CH_2$—, —$O(CH_2)PCH_2$—, —$O(CH_2)_qO$—, —$CH_2CH_2OCH_2CH_2$—, or —$CH_2CH_2NR^6CH_2CH_2$—, where n is 1 to 5; p is 1 to 4; and q is 1 to 4. $R^3$ can be H, OH, $NH_2$, CN, halogen, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, or $COR^A$. $R^A$ can be H, $C_1$ to $C_6$ alkyl, substituted $C_1$ to $C_6$ alkyl, $C_1$ to $C_6$ alkoxy, substituted $C_1$ to $C_6$ alkoxy, $C_1$ to $C_6$ aminoalkyl, or substituted $C_1$ to $C_6$ aminoalkyl. $R^4$ can be H, $C_1$ to $C_6$ alkyl, substituted $C_1$ to $C_6$ alkyl, $C_1$ to $C_6$ alkoxy, substituted $C_1$ to $C_6$ alkoxy, $C_1$ to $C_6$ aminoalkyl, or substituted $C_1$ to $C_6$ aminoalkyl. $R^5$ can be $C_1$ to $C_6$ alkyl, substituted $C_1$ to $C_6$ alkyl, or $COR^A$. $R^6$ can be H or $C_1$ to $C_6$ alkyl. X can be O, S, or absent. Q can be O or S, or a pharmaceutically acceptable salt thereof, by combining a base, a dialkyldithiophosphate, and a compound of formula II of the structure, or a pharmaceutically acceptable salt thereof, where $R^1$-$R^5$, Q, and X are defined above. See, Scheme 2.

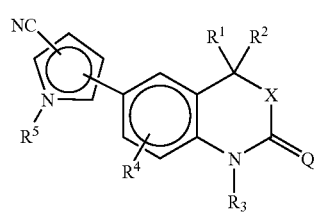

II

Scheme 2

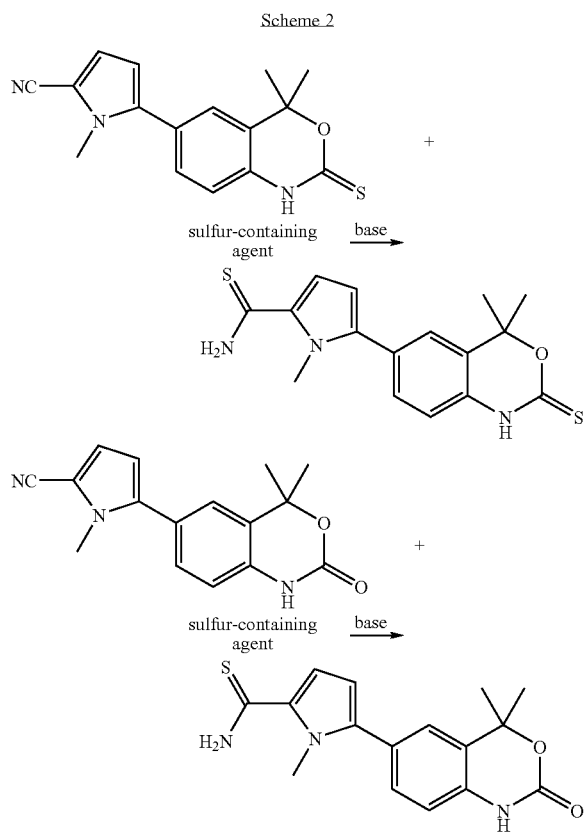

The method can further include purifying the compound of formula I including dissolving the compound of formula I in acetone to form a solution; heating the acetone solution to the boiling point of acetone; concentrating the acetone solution by distillation; and isolating the purified compound of formula I.

In a further embodiment, the present invention provides a method for preparing 6-(2-carbothioamide-pyrrole)-benzoxazine compounds, or pharmaceutically acceptable salts thereof, including reacting a 6-(2-cyanopyrrole)-benzoxazine compound, a base, and a sulfur-containing agent.

In another embodiment, the present invention provides a method for preparing 6-(2-carbothioamide-pyrrole)-benzoxazine compounds, or pharmaceutically acceptable salts thereof, including reacting a 6-(2-cyanopyrrole)-benzoxazine compound, a base, and a dialkyldithiophosphate.

In yet a further embodiment, the present invention provides a method for preparing 6-(2-carbothioamide-pyrrole)-benzoxazine compounds, or pharmaceutically acceptable salts thereof, including reacting a 6-(2-cyanopyrrole)-benzoxazine compound, a base, and hydrogen sulfide.

In still another embodiment, the present invention provides a method for preparing 6-(2-carbothioamide-pyrrole)-benzoxazine compounds, or pharmaceutically acceptable salts thereof, including reacting a 6-(2-cyanopyrrole)-benzoxazine compound, a base, and diethyldithiophosphate.

In yet another embodiment, the present invention provides a method for preparing 6-(2-carbothioamide-pyrrole)-benzoxazine compounds, or pharmaceutically acceptable salts thereof, including reacting a 6-(2-cyanopyrrole)-benzoxazine compound, Hünig's base, and diethyldithiophosphate.

In still a further embodiment, the present invention provides a method for preparing 6-(2-carbothioamide-pyrrole)-benzoxazin-2-one compounds, or pharmaceutically acceptable salts thereof, including reacting a 6-(2-cyanopyrrole)-benzoxazin-2-one compound, a base, and a dialkyldithiophosphate.

In yet another embodiment, the present invention provides a method for preparing 6-(2-carbothioamide-pyrrole)-benzoxazin-2-thione compounds, or pharmaceutically acceptable salts thereof, including reacting a 6-(2-cyanopyrrole)-benzoxazin-2-thione compound, a base, and a dialkyldithiophosphate.

In a further embodiment, the present invention provides a method for preparing 6-(2-carbothioamide-pyrrole)-benzoxazine compounds, or pharmaceutically acceptable salts thereof, including reacting a 6-(2-cyanopyrrole)-benzoxazine compound and hydrogen sulfide.

In still another embodiment, the present invention provides a method for preparing 6-(2-carbothioamide-pyrrole)-benzoxazine compound, or pharmaceutically acceptable salts thereof, including reacting a 6-(2-cyanopyrrole)-benzoxazine compound and diethyldithiophosphate.

IV. Methods of Using the Compounds of the Invention

The thioamide compounds of this invention are useful as progesterone receptor modulators, including antagonists and agonists. Specifically, the compounds of this invention can act as competitive inhibitors of progesterone binding to the PR and therefore act as agonists in functional models, either/or in-vitro and in-vivo.

The compounds utilized according to the present invention can contain one or more asymmetric centers and can thus give rise to optical isomers and diastereomers. While shown without respect to stereochemistry, the compounds can include optical isomers and diastereomers; racemic and resolved enantiomerically pure R and S stereoisomers; other mixtures of the R and S stereoisomers; and pharmaceutically acceptable salts thereof.

The compounds are therefore useful as oral contraceptives in both males and female. The compounds are also useful in hormone replacement therapy, and in preparing medicaments useful therefor. The compounds are further useful in the treatment of endometriosis, luteal phase defects, hormone-dependent neoplastic disease, and benign breast and prostatic diseases, and in preparing medicaments useful therefor. The hormone-dependent neoplastic disease can include uterine myometrial fibroids, endometriosis, benign prostatic hypertrophy, carcinomas and adenocarcinomas of the endometrium, ovary, breast, colon, prostate, pituitary, uterine, and meningioma. The compounds are also useful in treating hirsutism or acne, and in preparing medicaments useful therefor. The compounds are further useful in the synchronization of estrus, and in preparing medicaments useful therefor.

The compounds of this invention can be used alone as a sole therapeutic agent or can be used in combination with other agents, such as estrogens such as those described in US Patent Publication Nos. US-2004-0006122-A1 and US-2004-0014798-A1, which are hereby incorporated by reference, progestins, estrones, androgens, estrogen receptor agonist, or selective estrogen receptor modulators such as those described in US Patent Publication Nos. US-2004-0002535-A1 and US-2004-0006060-A1, which are hereby incorporated by reference.

The compounds of the present invention encompass tautomeric forms of the structures provided herein characterized by the bioactivity of the drawn structures. Further, the compounds of the present invention can be used in the form of pharmaceutically acceptable salts derived from pharmaceutically or physiologically acceptable acids, bases, alkali metals and alkaline earth metals.

Physiologically acceptable acids include those derived from inorganic and organic acids. A number of inorganic acids are known in the art and include hydrochloric, hydrobromic, hydroiodic, sulfuric, nitric, and phosphoric acids, among others. Similarly, a variety of organic acids are known in the art and include, without limitation, lactic, formic, acetic, fumaric, citric, propionic, oxalic, succinic, glycolic, glucuronic, maleic, furoic, glutamic, benzoic, anthranilic, salicylic, tartaric, malonic, mallic, phenylacetic, mandelic, embonic, methanesulfonic, ethanesulfonic, panthenoic, benzenesulfonic, toluenesulfonic, stearic, sulfanilic, alginic, and galacturonic acids, among others.

Physiologically acceptable bases include those derived from inorganic and organic bases. A number of inorganic bases are known in the art and include aluminum, calcium, lithium, magnesium, potassium, sodium, and zinc sulfate or phosphate compounds, among others. A number of organic bases are known in the art and include, without limitation, N,N,-dibenzylethylenediamine, chloroprocaine, choline, diethanolamine, ethylenediamine, meglumine, and procaine, among others.

Physiologically acceptable alkali salts and alkaline earth metal salts can include, without limitation, sodium, potassium, calcium and magnesium salts in the form of esters, and carbamates. Other conventional "pro-drug" forms can also be utilized which, when delivered in such form, convert to the active moiety in vivo.

These salts, as well as other compounds of the invention can be in the form of esters, carbamates and other conventional "pro-drug" forms, which, when administered in such form, convert to the active moiety in vivo. In a currently preferred embodiment, the prodrugs are esters. See, e.g., B. Testa and J. Caldwell, "Prodrugs Revisited: The "Ad Hoc" Approach as a Complement to Ligand Design", Medicinal Research Reviews, 16(3):233-241, ed., John Wiley & Sons (1996).

The compounds discussed herein also encompass "metabolites" which are unique products formed by processing the compounds of the invention by the cell or patient. In one embodiment, metabolites are formed in vivo.

The compounds of this invention can be formulated neat or with a pharmaceutical carrier for administration, the proportion of which is determined by the solubility and chemical nature of the compound, chosen route of administration and standard pharmacological practice. The pharmaceutical carrier may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets may contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g., cellulose derivatives, such as sodium carboxymethyl cellulose solution), alcohols (including monohydric alcohols and polyhydric alcohols, e.g., glycols) and their derivatives, lethicins, and oils (e.g., fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellant.

The compounds of the invention can be delivered by a route such as oral, dermal, transdermal, intrabronchial, intranasal, intravenous, intramuscular, subcutaneous, parenteral, intraperitoneal, intranasal, vaginal, rectal, sublingual, intracranial, epidural, intratracheal, or by sustained release. In one embodiment, delivery is oral or transdermal.

In one embodiment, the compositions are delivered orally by tablet, capsule, microcapsules, dispersible powder, granule, suspension, syrup, elixir, and aerosol. In another embodiment, when the compositions are delivered orally, delivery is by tablets and hard- or liquid-filled capsules.

In another embodiment, the compositions are delivered intravenously, intramuscularly, subcutaneously, parenterally and intraperitoneally in the form of sterile injectable solutions, suspensions, dispersions, and powders which are fluid to the extent that easy syringe ability exists. Such injectable compositions are sterile, stable under conditions of manufacture and storage, and free of the contaminating action of microorganisms such as bacteria and fungi.

Injectable formations can be prepared by combining the compositions with a liquid. The liquid can be selected from among water, glycerol, ethanol, propylene glycol and polyethylene glycol, oils, and mixtures thereof. In one embodiment, the liquid carrier is water. In another embodiment, the oil is vegetable oil. Optionally, the liquid carrier contains about a suspending agent. In another embodiment, the liquid carrier is an isotonic medium and contains about 0.05 to about 5% suspending agent.

In a further embodiment, the compositions are delivered rectally in the form of a conventional suppository.

In another embodiment, the compositions are delivered vaginally in the form of a conventional suppository, cream, gel, ring, or coated intrauterine device (IUD).

In yet another embodiment, the compositions are delivered intranasally or intrabronchially in the form of an aerosol.

In a further embodiment, the compositions are delivered transdermally or by sustained release through the use of a transdermal patch containing the composition and an optional carrier that is inert to the compound(s), is nontoxic to the skin, and allows for delivery of the compound(s) for systemic absorption into the blood stream. Such a carrier can be a cream, ointment, paste, gel, or occlusive device. The creams and ointments can be viscous liquid or semisolid emulsions. Pastes can include absorptive powders dispersed in petroleum or hydrophilic petroleum. Further, a variety of occlusive devices can be utilized to release the active reagents into the blood stream and include semi-permeable membranes covering a reservoir contain the active reagents, or a matrix containing the reactive reagents.

The use of sustained delivery devices can be desirable, in order to avoid the necessity for the patient to take medications on a daily basis. The term "sustained delivery" is used herein to refer to delaying the release of an active agent, i.e., compositions of the invention, until after placement in a delivery environment, followed by a sustained release of the agent at a later time. A number of sustained delivery devices are known in the art and include hydrogels (U.S. Pat. Nos. 5,266,325; 4,959,217; 5,292,515), osmotic pumps (U.S. Pat. Nos. 4,295,987 and 5,273,752 and European Patent No. 314,206, among others); hydrophobic membrane materials, such as ethylenemethacrylate (EMA) and ethylenevinylacetate (EVA); bioresorbable polymer systems (International Patent Publication No. WO 98/44964 and U.S. Pat. Nos. 5,756,127 and 5,854,388); and other bioresorbable implant devices composed of, for example, polyesters, polyanhydrides, or lactic acid/glycolic acid copolymers (U.S. Pat. No. 5,817,343). For use in such sustained delivery devices, the compositions of the invention can be formulated as described herein. See, U.S. Pat. Nos. 3,845,770; 3,916,899; 3,536,809; 3,598,123; and 4,008,719.

The dosage requirements vary with the particular compositions employed, the route of administration, the severity of the symptoms presented and the particular subject being treated. Based on the results obtained in the standard pharmacological test procedures, projected daily dosages of active compound would be about 0.1 to about 500 mg/kg, about 1 to about 100 mg/kg, about 2 to about 80 mg/kg, about 5 to about 50 mg/kg, or about 5 to about 25 mg/kg. Treatment will generally be initiated with small dosages less than the optimum dose of the compound. Thereafter the dosage is increased until the optimum effect under the circumstances is reached.

Advantageously, particularly potent PR modulators (e.g., those of formula I) may be useful at the lower end of the dosage ranges provided herein. The dosage regimen may however be adjusted to provide the optimal therapeutic response. For example, several divided doses (e.g., in divided doses 2 to 4 times a day) may be administered daily or the dose may be proportionally reduced as indicated by the exigencies of the therapeutic situation. Alternatively, a single dose can be delivered. In one embodiment, the delivery can be on a daily, weekly, or monthly basis. In another embodiment, delivery is daily. Daily dosages can be lowered or raised based on the periodic delivery.

Precise dosages for oral, parenteral, nasal, or intrabronchial administration can be determined by the administering physician based on experience with the individual subject treated. In one embodiment, the pharmaceutical composition is in unit dosage form, e.g., as tablets or capsules. In such form, the composition is sub-divided in unit dose containing appropriate quantities of the active ingredient; the unit dosage forms can be packaged compositions, for example, packaged powders, vials, ampoules, pre filled syringes or sachets containing liquids. The unit dosage form can be, for example, a capsule or tablet itself, or it can be the appropriate number of any such compositions in package form.

V. Pharmaceutical Kits

The present invention provides kits or packages of pharmaceutical formulations including the compounds of formula I described herein. When the compounds of formula I are to be delivered continuously, a package or kit can include the compound in each tablet. When the compound is to be delivered with periodic discontinuation, a package or kit can include placebos on those days when the compound is not delivered.

The kits can also be organized to indicate a single oral formulation or combination of oral formulations to be taken on each day of the cycle, in one embodiment including oral tablets to be taken on each of the days specified, and in another embodiment one oral tablet will contain each of the combined daily dosages indicated.

Similarly, other kits of the type described above may be prepared in which a compound of formula I is delivered. In one embodiment, the daily dosage of the compound of formula I remains fixed in each particular phase in which it is delivered. It is further preferable that the daily dose units described are to be delivered in the order described, with the first phase followed in order by the second and third phases. To help facilitate compliance with each regimen, it is also preferred that the kits contain the placebo described for the final days of the cycle.

The kits can also include an agent such as one or more of an agent selected from among estrogen, progestin, estrone, androgen, estrogen receptor agonist, or selective estrogen receptor modulator. One of skill in the art would readily be able to formulate a suitable amount of the above-noted agent for use in the kits of the invention.

A number of packages or kits are known in the art for the use in dispensing pharmaceutical agents for oral use. In one embodiment, the package has indicators for each day. In a further embodiment, the package is a labeled blister package, dial dispenser package, or bottle.

The following examples are provided to illustrate the invention and do not limit the scope thereof. One skilled in the art will appreciate that although specific reagents and conditions are outlined in the following examples, modifications can be made which are meant to be encompassed by the spirit and scope of the invention.

EXAMPLES

Example 1

Preparation of 5-(4,4-dimethyl-2-thioxo-1,4-dihydro-2H-3,1-benzoxazin-6-yl)-1-methyl-1H-pyrrole-2-carbothioamide In a 500-mL round-bottomed flask equipped with a magnetic stirrer, thermometer, addition funnel, and a reflux condenser, 5-(4,4-dimethyl-2-thioxo-1,4-dihydro-2H-3,1-benzoxazin-6-yl)-1-methyl-1H-pyrrole-2-carbonitrile (29.3 g, 98.6 mmol) was suspended in 1,2-dimethoxyethane (DME; 200 mL). Hünig's base (1 mL, 0.747 g, 5.75 mmol) was added followed by water (1 mL, 1.00 g, 55.6 mmol) and the mixture was heated to reflux. Diethyl dithiophosphate (49.0 g, 263 mmol, Aldrich, tech.) was added dropwise. The mixture turned homogenous after 15 minutes of heating and reaching 84° C. Eight minutes later, the temperature had reached 90° C. and solids started to precipitate. The high performance liquid chromatograph (HPLC) graph of the liquid phase sampled after 5 hours showed a 20/80 ratio of substrate/product. More diethyl dithiophosphate (11.0 g, 59 mmol) was added and the mixture was heated for an additional 30 minutes. The heating was thereby turned off and the mixture was stirred at room temperature for 20 hours, cooled, and filtered. A yellow solid was obtained (16.6 g; 51% crude yield; HPLC area %; 12/81 substrate/product).

A 5-L round-bottomed flask equipped with a mechanical stirrer and a reflux condenser was charged with the isolated solid (16.5 g) and acetone (2700 mL) was added in portions via the condenser while the suspension was heated to reflux. The reflux condenser was replaced with a regular one and acetone was distilled off. After distilling 2130 mL of acetone, the formed slurry was cooled to room temperature, stirred overnight, and filtered on a sintered-glass funnel to give a dark-yellow, crystalline, sandy solid. The filtered solid was dried at 40° C. in vacuo to give 12.5 g (76% recrystallization yield; 38% total yield) of 5-(4,4-dimethyl-2-thioxo-1,4-dihydro-2H-3,1-benzoxazin-6-yl)-1-methyl-1H-pyrrole-2-carbothioamide. LC purity: 95.94%; 1.65% NSP-989; rrt 0.88. LC-MS: 331 (M$^+$); impurity 297 (NSP-989). Mp: particles of various shapes; small particles melted 210-215° C.; next 218-220° C.; final melt 223-226° C. IR (KBr, cm$^{-1}$): 3375, 3269, 3165, 2211, 1624, 1610, 1540, 1526, 1466, 1370, 1294, 1261, 1186, 1114, 1086, 959, 880, 822, 779. $^1$H NMR (DMSO-d$_6$, ppm): 12.28 (s, 1H), 9.22 (s, 1H, S=CNH$_2$), 8.97 (s, 1H, S=CNH$_2$), 7.41 (d, 1H, J=7.05 Hz), 7.40 (s, 1H), 7.12 (d, 1H, J=8.85 Hz), 6.72 (d, 1H, J=3.9 Hz), 6.23 (d, 1H, J=3.9 Hz), 3.83 (s, 3H), 1.68 (s, 6H). The solids were sparingly soluble in dimethylsulfoxide (DMSO). $^{13}$C NMR (DMSO-d$_6$, ppm): 189.3 ((NH$_2$)C=S), 183.1 (HN(O)C=S), 140.6, 138.5, 135.2, 131.5, 129.8, 128.6, 127.2, 124.4, 114.8, 112.7, 108.4, 83.7, 35.8, 27.6.

Example 2

Preparation of 5-(4,4-dimethyl-2-oxo-1,4-dihydro-2H-3,1-benzoxazin-6-yl)-1-methyl-1H-pyrrole-2-carbothioamide This compound was prepared by following the procedure of Example 1 using 5-(4,4-dimethyl-2-oxo-1,4-dihydro-2H-3,1-benzoxazin-6-yl)-1-methyl-1H-pyrrole-2-carbonitrile (1.45 g) to give 5-(4,4-dimethyl-2-oxo-1,4-dihydro-2H-3,1-benzoxazin-6-yl)-1-methyl-1H-pyrrole-2-carbothioamide (0.79 g, 49% yield). $^1$H NMR (DMSO-d$_6$, ppm): 9.17 (s, 1H, S=CNH$_2$), 8.93 (s, 1H, S=CNH$_2$).

Example 3

Preparation of 5-(2'-thioxospiro[cylcohexane-1,3'-[3H]-indol]-5'-yl)-1-methyl-1H-pyrrole-2-carbothiomide This compound was prepared by following the procedure of Example 1 using 5-(2'-thioxospiro[cyclohexane-1,3'-[3H]-indol]-5'-yl)-1-methyl-1H-pyrrole-2-carbonitrile (1.45 g) to give 5-(2'-thioxospiro[cyclohexane-1,3'-[3H]-indol]-5'-yl)-1-methyl-1H-pyrrole-2-carbothioamide (0.20 g, 55% yield). $^1$H NMR (DMSO-d$_6$, ppm): 9.24 (s, 1H, S=CNH$_2$), 8.96 (s, 1H, S=CNH$_2$).

Example 4

Pharmacology 5-(4,4-dimethyl-2-thioxo-1,4-dihydro-2H-3,1-benzoxazin-6-yl)-1-methyl-1H-pyrrole-2-carbothioamide (1) and 5-(4,4-dimethyl-2-oxo-1,4-dihydro-2H-3,1-benzoxazin-6-yl)-1-methyl-1H-pyrrole-2-carbothioamide (2) were tested in a T47D cytosol alkaline phosphatase assay (Table 1). The purpose of this functional assay was to identify progestins or antiprogestins by determining the compound's effect on alkaline phosphatase activity in T47D cells.

TABLE 1

| Compound | % Efficacy | EC$_{50}$ (nM) |
|---|---|---|
| 1 | 60% | 0.2 |
| 2 | 72% | 1.9 |

(i) Culture Medium:
DMEM:F12 (1:1) (GIBCO, BRL) supplemented with 5% (v/v) charcoal stripped fetal bovine serum (not heat-inactivated), 100 U/mL penicillin, 100 μg/mL streptomycin, and 2 mM the GlutaMax™ reagent (GIBCO, BRL).

(ii) Alkaline Phosphatase Assay Buffer:
I. 0.1 M Tris-HCl, pH 9.8, containing 0.2% the Triton™ reagent X-100
II. 0.1 M Tris-HCl, pH 9.8 containing 4 mM p-nitrophenyl phosphate (Sigma).

(iii) Cell Culture and Treatment:
Frozen T47D cells were thawed in a 37° C. water bath and diluted to 280,000 cells/mL in culture medium. To each well in a 96-well plate (Falcon, Becton Dickinson Labware), 180 μL of diluted cell suspension was added. Twenty μL of reference or test compounds diluted in the culture medium was then added to each well. When testing for progestin antagonist activity, reference anti-progestins or test compounds were added in the presence of 1 nM progesterone. The cells were incubated at 37° C. in a 5% CO$_2$/humidified atmosphere for 24 hours.

(iv) Alkaline Phosphatase Enzyme Assay:
At the end of treatment, the medium was removed from the plate and 50 μL of assay buffer I was added to each well. The plates were shaken in a titer plate shaker for 15 minutes. Then 150 μL of assay buffer II was added to each well. Optical density measurements were taken at 5 minute intervals for 30 minutes at a test wavelength of 405 nM.

(v) Analysis of Results:
Analysis of dose-response data: For reference and test compounds, a dose response curve is generated for dose (X-axis) vs. the rate of enzyme reaction (slope) (Y-axis). Square root-transformed data are used for analysis of variance and nonlinear dose response curve fitting for both agonist and antagonist modes. Huber weighting is used to downweight the effects of outliers. EC$_{50}$ or IC$_{50}$ values are calculated from the retransformed values. JMP software (SAS Institute, Inc.) is used for both one-way analysis of variance and non-linear dose response analyses in both single dose and dose response studies.

(vi) Reference Compounds:
Progesterone and trimegestone are reference progestins and RU486 was the reference antiprogestin. All reference compounds are run in full dose response curves and the EC$_{50}$ or IC$_{50}$ values calculated.

TABLE 2

Estimated EC$_{50}$, standard error (SE), and 95% confidence intervals (CI) for reference progestins from three independent experiments

| | | | | 95% CI | |
|---|---|---|---|---|---|
| Compound | Exp. | EC$_{50}$ (nM) | SE | lower | upper |
| Progesterone | 1 | 0.839 | 0.030 | 0.706 | 0.996 |
| | 2 | 0.639 | 0.006 | 0.611 | 0.669 |
| | 3 | 1.286 | 0.029 | 1.158 | 1.429 |

TABLE 2-continued

Estimated EC$_{50}$, standard error (SE), and 95% confidence intervals (CI) for reference progestins from three independent experiments

| Compound | Exp. | EC$_{50}$ (nM) | SE | 95% CI lower | 95% CI upper |
|---|---|---|---|---|---|
| Trimegestone | 1 | 0.084 | 0.002 | 0.076 | 0.091 |
| | 2 | 0.076 | 0.001 | 0.072 | 0.080 |
| | 3 | 0.160 | 0.004 | 0.141 | 0.181 |

TABLE 3

Estimated IC$_{50}$, standard error, and 95% confident interval for the reference antiprogestin RU486 from three independent experiments

| Compound | Exp | IC$_{50}$ (nM) | SE | 95% CI lower | 95% CI upper |
|---|---|---|---|---|---|
| RU486 | 1 | 0.103 | 0.002 | 0.092 | 0.115 |
| | 2 | 0.120 | 0.001 | 0.115 | 0.126 |
| | 3 | 0.094 | 0.007 | 0.066 | 0.134 |

All publications listed in this specification are incorporated herein by reference herein. While the invention has been described with reference to a particularly preferred embodiment, it will be appreciated that modifications can be made without departing from the spirit of the invention. Such modifications are intended to fall within the scope of the appended claims.

The invention claimed is:

1. A compound of formula I of the structure:

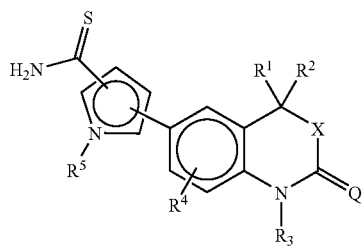

I wherein:
R$^1$ and R$^2$ are, independently, H, C$_1$ to C$_6$ alkyl, or substituted C$_1$ to C$_6$ alkyl;
or R$^1$ and R$^2$ are fused to form a ring comprising —CH$_2$(CH$_2$)$_n$CH$_2$—, —CH$_2$CH$_2$C(CH$_3$)$_2$CH$_2$CH$_2$—, —O(CH$_2$)$_p$CH$_2$—, —O(CH$_2$)$_q$O—, —CH$_2$CH$_2$OCH$_2$CH$_2$—, or —CH$_2$CH$_2$NR$^6$CH$_2$CH$_2$—;
n is to 5;
p is 1 to 4;
q is 1 to 4;
R$^3$ is H, OH, NH$_2$, CN, halogen, C$_1$ to C$_6$ alkyl, substituted C$_1$ to C$_6$ alkyl, C$_2$ to C$_6$ alkenyl, substituted C$_2$ to C$_6$ alkenyl, C$_2$ to C$_6$ alkynyl, substituted C$_2$ to C$_6$ alkynyl, or COR$^4$;
R$^4$ is H, C$_1$ to C$_6$ alkyl, substituted C$_1$ to C$_6$ alkyl, C$_1$ to C$_6$ alkoxy, substituted C$_1$ to C$_6$ alkoxy, C$_1$ to C$_6$ aminoalkyl, or substituted C$_1$ to C$_6$ aminoalkyl;
R$^5$ is C$_1$ to C$_6$ alkyl, substituted C$_1$ to C$_6$ alkyl, or COR$^4$;
R$^6$ is H or C$_1$ to C$_6$ alkyl;
X is absent;
Q is O or S;
or a pharmaceutically acceptable salt thereof.

2. The compound of formula I according to claim 1, wherein R$^1$ and R$^2$ are CH$_3$ or are fused to form a ring comprising —CH$_2$(CH$_2$)$_n$CH$_2$—.

3. The compound of formula I according to claim 2, wherein n is 3.

4. The compound of formula I according to claim 1, wherein R$^3$ or R$^4$ is H.

5. The compound of formula I according to claim 1, wherein X is absent.

6. The compound of formula I according to claim 1, wherein the pyrrole ring is a 2,5-substituted pyrrole.

7. The compound of formula I according to claim 1, which is 5-(2'-thioxospiro[cyclohexane-1,3'-[3H]-indol]-5'-yl)-1-methyl-1H-pyrrole-2-carbothioamide; or a pharmaceutically acceptable salt thereof.

8. A pharmaceutical composition comprising a compound of formula I of claim 1, or a pharmaceutically acceptable salt thereof, and a pharmaceutically acceptable carrier or excipient.

9. A method for preparing a compound of formula I of claim 1, said method comprising reacting a sulfur-containing agent and a compound of formula II of the structure:

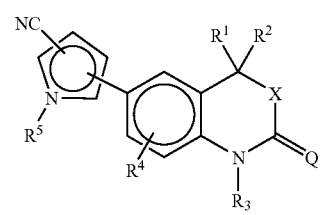

II or a pharmaceutically acceptable salt thereof in the presence of a base.

10. The method according to claim 9, wherein said sulfur-containing agent is a dialkyldithiophosphate or H$_2$S.

11. The method according to claim 10, wherein the ratio of said dialkyldithiophosphate to said compound of formula II is about 1:1 to about 3:1.

12. The method according to claim 10, wherein said dialkyldithiophosphate is diethyl dithiophosphate.

13. The method according to claim 9, wherein said base is an amine.

14. The method according to claim 9, wherein said compound of formula I is purified comprising:
(a) dissolving said compound of formula I in acetone to form a solution;
(b) heating said acetone solution to the boiling point of acetone;
(c) concentrating said acetone solution by distillation; and
(d) isolating said purified compound of formula I.

15. The method according to claim 14, further comprising dimethoxyethane.

16. The method according to claim 15, wherein said dimethoxyethane is heated to its boiling point.

17. A method for contraception, treating dysfunctional bleeding, treating polycystic ovary syndrome, treating acne, or treating hirsutism, said method comprising administering to a mammal in need thereof a compound of formula I of the following structure:

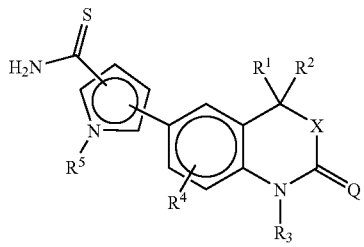

wherein:
$R^1$ and $R^2$ are, independently, H, $C_1$ to $C_6$ alkyl, or substituted $C_1$ to $C_6$ alkyl;
or $R^1$ and $R^2$ are fused to form a ring comprising —$CH_2(CH_2)_nCH_2$—, —$CH_2CH_2C(CH_3)_2CH_2CH_2$—, —$O(CH_2)_pCH_2$—, —$O(CH_2)_qO$—, —$CH_2CH_2OCH_2CH_2$—, or —$CH_2CH_2NR^6CH_2CH_2$—;
n is 1 to 5;
p is 1 to 4;
q is 1 to 4;
$R^3$ is H, OH, $NH_2$, CN, halogen, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, or $COR^A$;
$R^A$ is H, $C_1$ to $C_6$ alkyl, substituted $C_1$ to $C_6$ alkyl, $C_1$ to $C_6$ alkoxy, substituted $C_1$ to $C_6$ alkoxy, $C_1$ to $C_6$ aminoalkyl, or substituted $C_1$ to $C_6$ aminoalkyl;
$R^4$ is H, $C_1$ to $C_6$ alkyl, substituted $C_1$ to $C_6$ alkyl, $C_1$ to $C_6$ alkoxy, substituted $C_1$ to $C_6$ alkoxy, $C_1$ to $C_6$ aminoalkyl, or substituted $C_1$ to $C_6$ aminoalkyl;
$R^5$ is $C_1$ to $C_6$ alkyl, substituted $C_1$ to $C_6$ alkyl, or $COR^A$;
$R^6$ is H or $C_1$ to $C_6$ alkyl;
X is absent;
Q is O or S;
or a pharmaceutically acceptable salt thereof.

18. A pharmaceutical kit useful for contraception, treating dysfunctional bleeding, treating uterine leiomyomata, treating endometriosis, treating polycystic ovary syndrome, treating acne, or treating hirsutism, said kit comprising a compound of formula I of the structure:

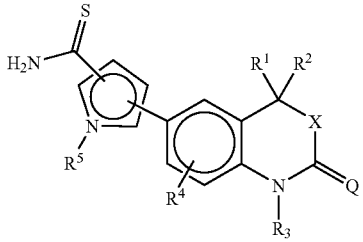

wherein:
$R^1$ and $R^2$ are, independently, H, $C_1$ to $C_6$ alkyl, or substituted $C_1$ to $C_6$ alkyl;
or $R^1$ and $R^2$ are fused to form a ring comprising —$CH_2(CH_2)_nCH_2$—, —$CH_2CH_2C(CH_3)_2CH_2CH_2$—, —$O(CH_2)_pCH_2$—, —$O(CH_2)_qO$—, —$CH_2CH_2OCH_2CH_2$—, or —$CH_2CH_2NR^6CH_2CH_2$—;
n is 1 to 5;
p is 1 to 4;
q is 1 to 4;
$R^3$ is H, OH, $NH_2$, CN, halogen, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, or $COR^A$;
$R^A$ is H, $C_1$ to $C_6$ alkyl, substituted $C_1$ to $C_6$ alkyl, $C_1$ to $C_6$ alkoxy, substituted $C_1$ to $C_6$ alkoxy, $C_1$ to $C_6$ aminoalkyl, or substituted $C_1$ to $C_6$ aminoalkyl;
$R^4$ is H, $C_1$ to $C_6$ alkyl, substituted $C_1$ to $C_6$ alkyl, $C_1$ to $C_6$ alkoxy, substituted $C_1$ to $C_6$ alkoxy, $C_1$ to $C_6$ aminoalkyl, or substituted $C_1$ to $C_6$ aminoalkyl;
$R^5$ is $C_1$ to $C_6$ alkyl, substituted $C_1$ to $C_6$ alkyl, or $COR^A$;
$R^6$ is H or $C_1$ to $C_6$ alkyl;
X is absent;
Q is O or S;
or a pharmaceutically acceptable salt thereof.

19. The kit according to claim 18, further comprising an estrogen, progestin, estrone, androgen, estrogen receptor agonist, or selective estrogen receptor modulator.

* * * * *